(12) United States Patent
Gillman et al.

(10) Patent No.: US 6,916,937 B2
(45) Date of Patent: Jul. 12, 2005

(54) CARBOHYDRATE PRODRUGS OF FLUOROOXINDOLES

(75) Inventors: Kevin Gillman, Madison, CT (US); Danielle M. Bocchino, New Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/762,907

(22) Filed: Jan. 22, 2004

(65) Prior Publication Data

US 2004/0152646 A1 Aug. 5, 2004

Related U.S. Application Data

(60) Provisional application No. 60/444,425, filed on Feb. 3, 2003.

(51) Int. Cl.[7] .............................. C07F 9/02; C07F 9/547

(52) U.S. Cl. ........................ 548/414; 514/419; 514/43; 536/17.4

(58) Field of Search .................. 514/419, 43; 548/414; 536/17.4

(56) References Cited

U.S. PATENT DOCUMENTS

| | | | |
|---|---|---|---|
| 5,602,169 A | | 2/1997 | Hewawasam et al. |
| 2002/0156120 A1 | * | 10/2002 | Hewawasam et al. ...... 514/419 |
| 2003/0195169 A1 | * | 10/2003 | Gillman et al. ............. 548/414 |

FOREIGN PATENT DOCUMENTS

WO  WO 93/08800  5/1993

OTHER PUBLICATIONS

Faber et al., "Calcium–activated potassium channels: Multiple contributions to neuronal function," The neuroscientist, 2003, vol. 9, No. 3, pp. 181–185.*

Xia et al., "Multiple regulatory sites in large–conductance calcium–activated potassium channels," Nature, 2002, vol. 418, pp. 880–884.*

Zhang et al., "Amide N–Glucoronidation of maxipost catalyzed by UDP–Glucuronosyltransferase 2B7 in humans," Pharamceutical Candidate Optimization, Pharmaceutical research institute, 2004.*

Calderone V., "Large–conductance ca(2+) activated k(+) channels: function, pharmacology and drugs," Curr Med Chem, 2002, vol. 14, pp. 1385–1395.*

Nardi et al., "Natural modulators of large–conductance calcium–activated potassium channels," Planta Med., 2003, vol. 10, pp. 885–892.

Meredith et al., "Overactive bladder and incontinence in the absence of the BK large conductance Ca2+–activated K+ channel," J. Biol. Chem., 2004, vol. 269, Issue 35, pp. 746–752.

Sausbier et al., "Cerebellar ataxia and Purkinje cell dysfunction caused by Ca2+ activated K+ channel deficiency," Proc Natl Acad Sci, 2004, vol. 101, pp. 9474–9478.

Greffrath et al., "Contribution of Ca2+–activated K+ channels to hyperpolarizing potentials and discharge pattern in rat supraoptic neurones," J. Neuroendocrinol, 2004, vol. 7, pp. 577–588.

Xi et al., "Carbon monoxide activates KCa channels in newborn arteriole smooth muscle cells by increasing apparent Ca2+ sensitivity of alpha subunits," Am J Physiol Heart Circ Physiol, 2004, vol. 6.*

Cook, Nigel S., "The pharmacology of potassium channels and their therapeutic potential," TIPS, Jan. 1998, vol. 9, pp. 21–28.

Quast, Ulrich et al., "Moving together: K+ channel openers and ATP–sensitive K+ channels," TIPS Nov. 1989, vol. 10, pp. 431–435.

Singer, Joshua J. et al., "Characerization of calcium–activated potassium channels in single smooth muscle cells using the patch clamp technique," Pflügers Arch., 1987, vol. 408, pp. 98–111.

Baro, I. et al., "A Ca2+–activated K+ current in guinea–pig atrial myocytes," Pflügers Arch., 1989, vol. 414, Supp. 1, pp. S168–S170.

(Continued)

*Primary Examiner*—James O. Wilson
*Assistant Examiner*—Jason H. Johnsen
(74) *Attorney, Agent, or Firm*—Richard P. Ryan

(57) ABSTRACT

The present invention provides novel prodrug derivatives of fluorooxindoles having the general Formula I

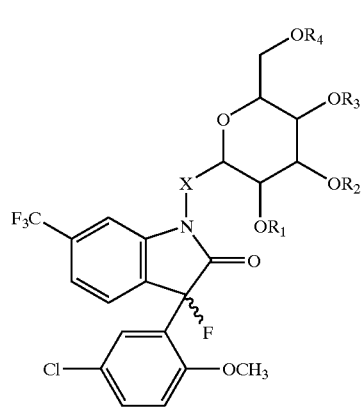

wherein the wavy bond (∿) represents the racemate, the (R)-enantiomer or the (S)-enantiomer, and $R^1$, $R^2$, $R^3$, $R^4$ and X are as defined herein, or a nontoxic pharmaceutically acceptable salt or solvate thereof and are useful in the treatment of disorders which are responsive to the opening of potassium channels.

8 Claims, No Drawings

OTHER PUBLICATIONS

Ahmed, F. et al., "Some features of the spasmogenic actions of acetylcholine and histamine in guinea–pig isolated trachealis," Br. J. Pharmac., 1984, vol. 83, pp. 227–233.

Trivedi, S. et al., "Calcium dependent K–channels in guinea pig and human urinary bladder," Biochemical and Biophysical Research Communications, 1995, vol. 213, No. 2, pp. 404–409.

Koh, Duk–Su et al., Effect of the flavoid phloretin on $Ca^{2+}$–activated $K+$ channels in myelinated nerve fibres of Xenopus laevis, Neuroscience Letters, 1994, vol. 165, pp. 167–170.

Leu, Yu–Ling et al., "Design and synthesis of water–soluble glucuronide derivaties of camptothecin for cancer prodrug monotherapy and antibody–directed enzyme prodrug therapy (ADEPT)," J. Med. Chem., 1999, vol. 42, pp. 3623–2628.

Truelove, J.E. et al., "Synthesis of 1–O–(2'–acetoxy)-benzoyl–α–D–2–deoxyglucopyranose, a novel aspirin prodrug," Journal of Pharmaceutical Sciences, Feb. 1980, vol. 69, No. 2 pp. 231–232.

Varia, S.A. et al., "Phenytoin prodrugs III: water–soluble prodrugs for oral and/or parenteral use," Journal of Pharmaceutical Sciences, Aug. 1984, vol. 73, No. 8, pp. 1068–1073.

Gribkoff, V.K.. et al., "Targeting acute ischemic stroke with a calcium–sensitive opener of maxi–K potassium channels," Nature Medicine, Apr. 2001, vol. 7, No. 4, pp. 471–477.

* cited by examiner

CARBOHYDRATE PRODRUGS OF FLUOROOXINDOLES

CROSS REFERENCE TO RELATED APPLICATIONS

The present application claims the benefit of priority under 35 U.S.C. § 119(e) from the provisional application 60/444,425 filed Feb. 3, 2003.

FIELD OF THE INVENTION

The present invention is directed to novel prodrug derivatives of a fluorooxindole compound which is a modulator of the large-conductance calcium-activated potassium (BK) channels and, therefore, useful in the protection of neuronal cells and diseases arising from dysfunction of cellular membrane polarization and conductance. The present invention also provides a method of treatment with the novel substituted fluorooxindole derivatives and to pharmaceutical compositions thereof.

BACKGROUND OF THE INVENTION

Stroke is presently recognized as the third leading cause of adult disability and death in the United States and Europe. In the past decade, several therapeutic approaches for the minimization of stroke-related brain damage have been pursued including inhibitors of AMPA/kainate, N-methyl-D-aspartate (NMDA) and adenosine reuptake inhibitors. It is the object of the present invention to provide novel compounds that will modulate potassium channels, in particular, large-conductance calcium-activated potassium (BK) channels which will be useful in reducing neuronal damage during ischemic conditions of a stroke episode.

Potassium channels play a key role in regulation of cell membrane potential and modulation of cell excitability. Potassium channels are themselves regulated by voltage, cell metabolism, calcium ion and receptor mediated processes. [Cook, N. S., *Trends in Pharmacol. Sciences*, 9, pp. 21–28 (1988); and Quast, U. and Cook, N. S., *Trends in Pharmacol. Sciences*, 10, pp. 431–435 (1989)]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance <50 pS. ("pS" stands for picosiemen, a unit of electrical conductance.) Large-conductance calcium-activated potassium (BK) channels are present in many excitable cells including neurons, cardiac cells and various types of smooth muscle cells. [Singer, J. J. and Walsh, J. V., *Pflügers Archiv.*, 408, pp. 98–111 (1987); Baró, I., and Escande, D., *Pflügers Archiv.*, 414 (Suppl. 1), pp. S168–S170 (1989); and Ahmed, F. et al., *Br. J. Pharmacol.*, 83, pp. 227–233 (1984)].

Potassium ions play a dominant role in controlling the resting membrane potential in most excitable cells and in maintaining the transmembrane voltage near the $K^+$ equilibrium potential ($E_k$) of about −90 mV. It has been shown that opening of potassium channels shifts the cell membrane potential towards the equilibrium potassium membrane potential ($E_k$), resulting in hyperpolarization of the cell. [Cook, N. S., *Trends in Pharmacol. Sciences*, 9, pp. 21–28 (1988]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells under ischemic conditions.

The role of potassium channels in the operation of the smooth muscle of the human urinary bladder is discussed by S. Trivedi, et al. in *Biochemical and Biophysical Research Communications*, (1995), 213, No.2, pp. 404–409.

A range of synthetic and naturally occurring compounds with BK opening activity have been reported. The *avena* pyrone extracted from *avena sativa*-common oats has been identified as a BK channel opener using a lipid bi-layer technique [International Patent application WO 93/08800, published May 13, 1993]. The flavanoid, Phloretin has been found to affect the opening of $Ca^{2+}$-activated potassium channels in myelinated nerve fibers of *Xenopus laevis* using outside-out patches [Koh, D-S., et al., *Neuroscience Lett.*, 165, pp. 167–170 (1994)].

Glucuronide prodrugs of 9-aminocamptothecin were disclosed by Leu in *J.Med. Chem.* 42, 3623–3628 (1999) in which glucuroinide was linked through a benzyloxycarbamate spacer to 9-campothecin. The prodrug increased the solubility of 9-aminocamptothecin and could be cleaved in vitro to liberate 9-aminocamptothecin.

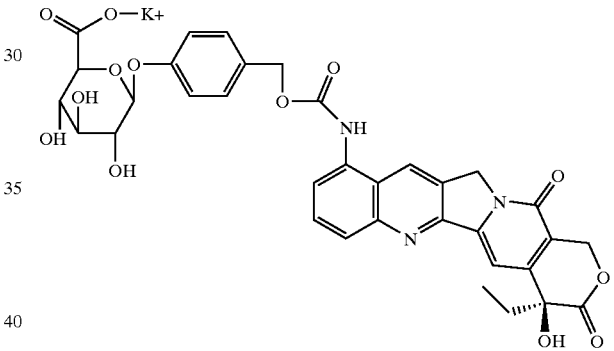

Truelove showed that 2-deoxyglucose could be coupled to 2-acetoxybenzoic acid (aspirin) to prepare a prodrug which could be cleaved in vitro to liberate aspirin in *J. Pharm. Sci.* 69, pp. 231–232 (1980).

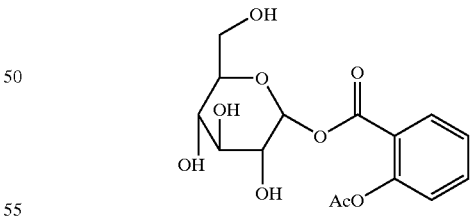

Varia disclosed the use of phosphonomethoxy derivatives as prodrugs of the hydantoin Phenytoin in *J. Pharm. Sci.* 73, pp. 1068–1073 (1984).

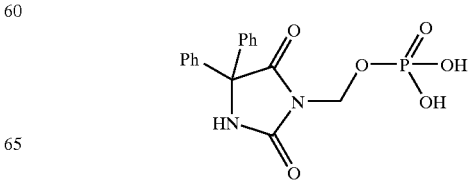

Hewawasam, et al. demonstrated in U.S. Pat. No. 5,602,169 that (3S)-(−)-(5-Chloro-2-methoxyphenyl)-1,3-dihydro-3-fluoro-6-(trifluoromethyl)-2H-indol-2-one is a modulator of large-conductance, calcium-activated potassium (BK) channels, and is useful for the treatment of ischemia.

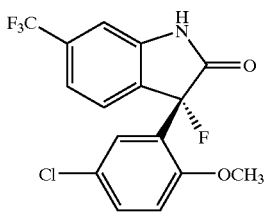

Hewawasam et. al. (U.S. Pat. No. 5,602,169) describe the synthesis of the above compound and its utility to treat disorders sensitive to potassium channel opening, including cerebral ischemia and traumatic brain injury. Due to the low aqueous solubility of the above compound, additives such as dimethylsulfoxide and propylene glycol, for example, must be employed in order to prepare solutions of the compound of Formula I suitable for intravenous injection (Gribkoff, et al., *Nature Medicine*, 2001, 7, 471–477).

SUMMARY OF THE INVENTION

The present invention provides novel prodrug derivatives of 3-fluorooxindoles having the general formula

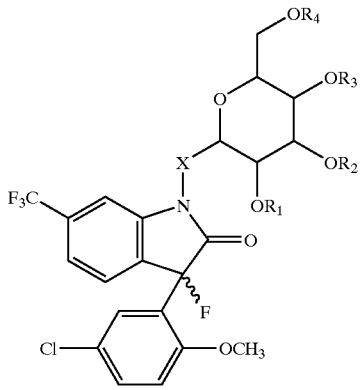

wherein the wavy bond (∼) represents the racemate, the (R)-enantiomer or the (S)-enantiomer and $R_1$, $R_2$, $R_3$ and $R_4$ and X are as defined below, or a nontoxic pharmaceutically acceptable salt or solvate thereof. The carbohydrate moieties, which are optimally phosphorylated, provide the prodrugs of the present invention which increase the water solubility of the 3-fluorooxindoles, and thereby decrease the amount of additives that need to be employed to deliver an intravenous dose of the oxindole. Upon systemic administration, the prodrug derivatives are transformed to liberate systemic levels of the fluorooxindole. The present invention also provides pharmaceutical compositions comprising said prodrug derivatives and to the method of treatment of disorders sensitive to potassium channel opening activity such as ischemia, stroke, convulsions, asthma, epilepsy, irritable bowel syndrome, migraine, traumatic brain injury, spinal cord injury, sexual dysfunction, carbon monoxide poisoning and urinary incontinence.

DETAILED DESCRIPTION OF THE INVENTION

The present invention provides novel prodrug derivatives of the racemate, the (R)-enantiomer and (S)-enantiomer of 3-(5-chloro-2-methoxyphenyl)-1,3-dihydro-3-fluoro-6-(trifluoromethyl)-2H-indol-2-one (compound of Formula II) which is a potent opener of the large conductance, calcium-activated K⁺-channels (BK channel) and the novel derivatives of the present invention have the general Formula I

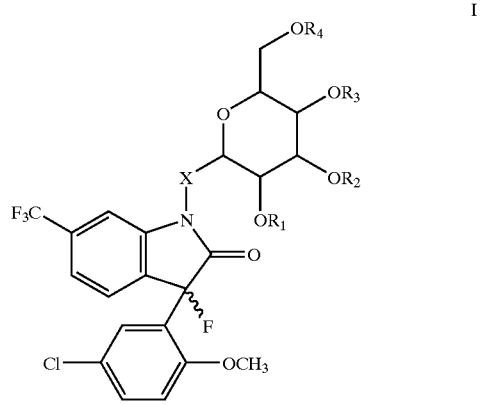

wherein the wavy bond (∼) represents the racemate, the (R)-enantiomer or the (S)-enantiomer;
$R_1$, $R_2$, $R_3$ and $R_4$ each are independently hydrogen or —P(O)OR⁵OR⁶;
$R^5$ and $R^6$ each are independently hydrogen or $C_{1-4}$ alkyl;
X is a covalent bond or —CR⁵R⁶O—;
or a nontoxic pharmaceutically acceptable salt or solvate thereof.

The present invention also provides a method for the treatment of or protection from disorders which are mediated by opening of the large conductance calcium-activated K⁺ channels (BK channels) in a mammal in need thereof, which comprises administering to said mammal a therapeutically effective amount of a compound of Formula I or a nontoxic pharmaceutically acceptable salt thereof. Preferably, the compounds of Formula I are useful in the treatment of ischemia, stroke, epilepsy, convulsions, asthma, irritable bowel syndrome, migraine, traumatic brain injury, spinal cord injury, sexual dysfunction, carbon monoxide poisoning and urinary incontinence and other disorders sensitive to BK channel activating activity.

The terms "$C_{1-4}$ alkyl" as used herein and in the claims (unless the context indicates otherwise) means straight or branched chain alkyl groups such as methyl, ethyl, propyl, isopropyl, and butyl. Preferably, these groups contain from 1 to 2 carbon atoms.

The term "a nontoxic pharmaceutically acceptable salt" as used herein and in the claims is intended to include nontoxic base addition salts with inorganic and organic bases. The salt of a Formula I compound which may be represented herein by M⊕ and includes the monoanionic, the dianionic and trianionic salts, for example, the mono sodium, the di sodium and the tri sodium salts. Suitable inorganic bases such as alkali and alkaline earth metal bases and could include metallic cations would be sodium, potassium, magnesium, calcium and the like. Suitable organic bases include amines such as ammonium, alkylamine, dialkylamine, trialkylamines, tetraalkylammonnium, pyridine, dibenzylamine, ethanolamine, N-methylglucamine, N-methylpiperidine, N-methylmorpholine, lysine, arginine and other amines which have been used to form salts of carboxylic acids and phosphoric acids.

Generally, pharmaceutically acceptable salts of the invention are those in which the counter-ion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula I compound wherein $R^1$–$R^6$ are hydrogen with the selected base, preferably by contact in solution employing an excess of commonly used inert solvents such as water, ether, acetonitrile, dioxane, methylene chloride, isopropanol, methanol, ethanol, ethyl acetate and acetonitrile. They may also be made by metathesis or treatment with an ion exchange resin under conditions in which the appropriate ion of a salt of the substance of the Formula I compound is replaced by another ion under conditions which allow for separation of the desired species such as by precipitation from solution or extraction into a solvent, or elution from or retention on an ion exchange resin.

Certain compounds of the present invention including the pharmaceutically acceptable salts thereof can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the composition that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

In another aspect, this invention provides water-soluble prodrugs of the compound of the racemate, the (R)-enantiomer and the (S)-enantiomer of 3-(5-chloro-2-methoxyphenyl)-1,3-dihydro-3-fluoro-6-(trifluoromethyl)-2H-indol-2-one which is described in U.S. Pat. No. 5,602,169. As used herein the term prodrug denotes a derivative of an active drug which is converted following systemic administration back to the active drug. More particularly, it refers to prodrug carbohydrate derivatives of 3-fluorooxindole drugs which may be in phosphate ester form and which are capable of undergoing hydrolysis to release active free drug. For example, the prodrugs may be hydrolyzed in the host to produce a more active form of the desired 3-fluorooxindole. The physiologically hydrolyzable groups also serve as prodrugs by being hydrolyzed in the body to yield the parent drug per se, and thus, the water-soluble prodrugs of the present invention are preferred for administration of the parent drug.

In still another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt, solvate or hydrate thereof. Preferably, the compounds of Formula I are useful in the treatment of ischemia, stroke, convulsions, epilepsy, asthma, irritable bowel syndrome, migraine, traumatic brain injury, spinal cord injury, carbon monoxide poisoning, urinary incontinence and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity. Most preferably, the compounds of Formula I are useful in the treatment of cerebral ischemia/stroke.

In still yet another aspect, this invention provides pharmaceutical compositions comprising at least one compound of Formula I in combination with a pharmaceutical adjuvant, carrier or diluent.

The compounds of Formula I may be prepared by various procedures such as those illustrated herein in the examples, in the Reaction Schemes and variations thereof which would be evident to those skilled in the art. The various prodrug compounds of Formula I may advantageously be prepared from the active drug substance of Formula II which is itself prepared by the general procedure described in U.S. Pat. No. 5,602,169 and used as the starting material in the methods illustrated in Reaction Schemes 1 to 3.

REACTION SCHEME 1

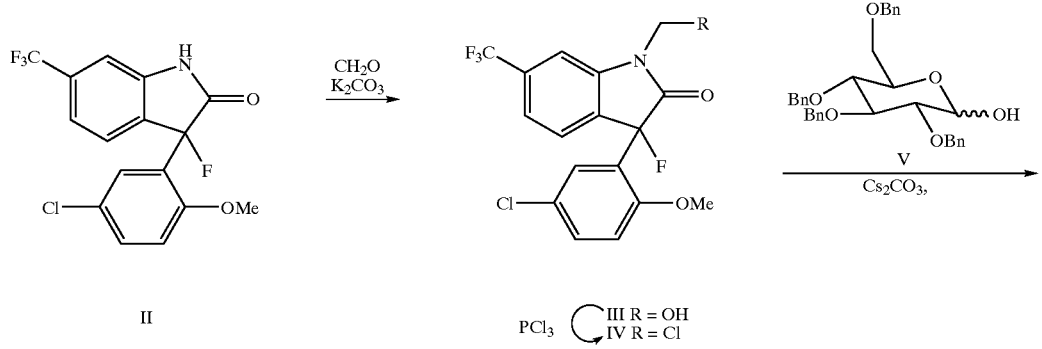

The preparation of the compounds of Formula Ia is depicted in Scheme I. Acylation of the compound of Formula II with an acylating agent such as formaldehyde affords the hydroxymethyl adduct of Formula III. Chlorination of the hydroxyl group with a halogenating agent such as phosphorous trichloride provides the chloromethyl lactam of Formula IV. Treatment of the chloromethyloxindole with a protected sugar such as Formula V with a free anomeric alcohol in the presence of a base such as cesium carbonate provides the protected sugar of Formula VI. Deprotection of the sugar under hydrogenation conditions affords the compound of Formula Ia.

To prepare the compounds of Formula Ib, the fluorooxindoles of Formula II were alkylated with epoxide of Formula VII in the presence of a base such as sodium hydride to afford the protected sugars of Formula VIII as shown in Scheme 2. The protection groups can be removed by hydrogenation to provide the compounds of Formula Ib.

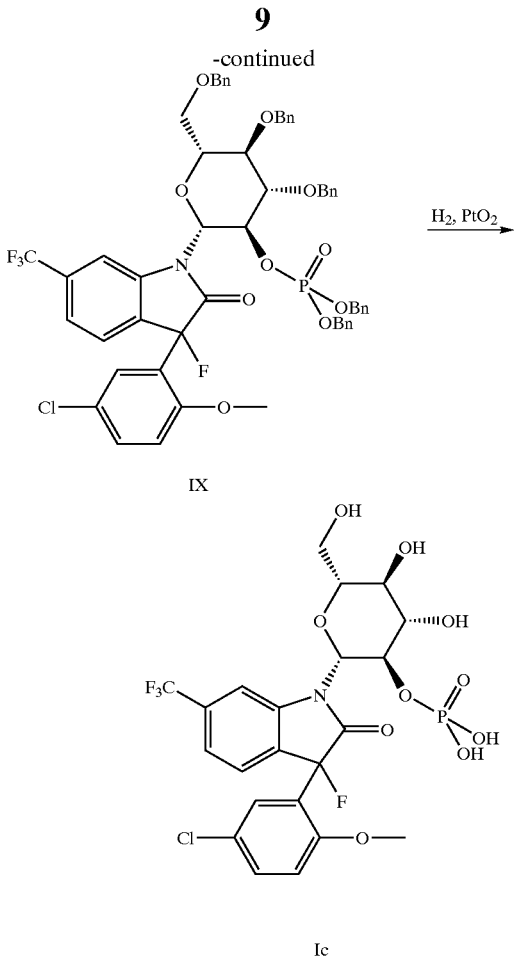

IX

Ic

Compounds of Formula Ic can be prepared as shown in Scheme 3. Treatment of an alcohol of Formula VIII with a phosphoramidate in the presence of base, followed by oxidation with hydrogen peroxide, afforded the phosphate of Formula IX. Deprotection by hydrogenation gave the carbohydrate of Formula Ic.

In a preferred embodiment of the invention, the compounds have the Formula I'

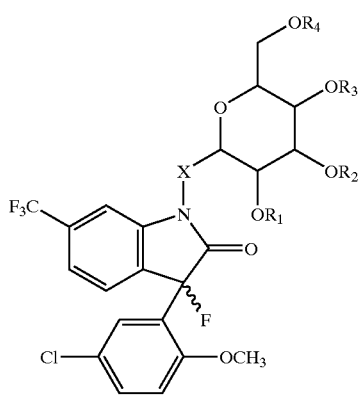

wherein the wavy bond (∿) represents the racemate, the (R)-enantiomer or the (S)-enantiomer;
$R_1$, $R_2$, $R_3$ and $R_4$ each are independently hydrogen or —P(O)OR$^5$OR$^6$;
$R^5$ and $R^6$ each are independently hydrogen or $C_{1-4}$ alkyl;
X is a covalent bond or —CR$^5$R$^6$O—;

or a nontoxic pharmaceutically acceptable salt or solvate thereof.

In a more preferred embodiment of the invention, the wavy bond (∿) represents the (S)-enantiomer in the compounds of Formula I'.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating ischemia, convulsions, epilepsy, asthma, irritable bowel syndrome, migraine, traumatic brain injury, spinal cord injury, carbon monoxide poisoning, male and female sexual dysfunction, urinary incontinence and especially stroke in a mammal in need thereof, which comprises administering to said mammal a therapeutically effective amount of a compound of Formula I or a nontoxic pharmaceutically acceptable salt, solvate or hydrate thereof.

Biological Activity

Potassium (K$^+$) channels are structurally and functionally diverse families of K$^+$-selective channel proteins which are ubiquitous in cells, indicating their central importance in regulating a number of key cell functions [Rudy, B., *Neuroscience*, 25, pp. 729–749 (1988)]. While widely distributed as a class, K$^+$ channels are differentially distributed as individual members of this class or as families. [Gehlert, D. R., et al., *Neuroscience*, 52, pp. 191–205 (1993)]. In general, activation of K$^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, K$^+$ channels can respond to important cellular events such as changes in the intracellular concentration of ATP or the intracellular concentration of calcium (Ca$^{2+}$). The central role of K$^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the large-conductance Ca$^{2+}$-activated K$^+$ channels (BK or BK channels), is regulated by transmembrane voltage, intracellular Ca$^{2+}$, and a variety of other factors such as the phosphorylation state of the channel protein. [Latorre, R., et al., *Ann. Rev. Physiol.*, 51, pp. 385–399 (1989)]. The large, single channel-conductance (generally >150 pS) and high degree of specificity for K$^+$ of BK channels indicates that small numbers of channels could profoundly affect membrane conductance and cell excitability. Additionally, the increase in open probability with increasing intracellular Ca$^{2+}$ indicates involvement of BK channels in the modulation of Ca$^{2+}$-dependent phenomena such as secretion and muscular contraction. [Asano, M., et al., *J. Pharmacol. Exp. Ther.*, 267, pp. 1277–1285 (1993)].

Openers of BK channels exert their cellular effects by increasing the open probability of these channels [McKay, M. C., et al., *J. Neurolphysiol.*, 71, pp.1873–1882 (1994); and Olesen, S.-P., *Exp. Opin. Invest. Drugs*, 3, pp. 1181–1188 (1994)]. This increase in the opening of individual BK channels collectively results in the hyperpolarization of cell membranes, particularly in depolarized cells, produced by significant increases in whole-cell BK-mediated conductance.

The ability of the compound of Formula II to open BK channels and increase whole-cell outward ($K^+$) BK-mediated currents was assessed under voltage-clamp conditions by determining their ability to increase cloned mammalian (mSlo or hSlo) BK—mediated outward current heterologously expressed in *Xenopus oocytes* [Butler, A., et al., *Science*, 261, pp. 221–224 (1993); and Dworetzky, S. I., et al., *Mol. Brain Res.*, 27, pp.189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., *J. Biol. Chem*, 265, pp.11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compound profiled did not effect non-BK native currents in the oocytes. The compound of Formula II was shown in at least 5 oocytes at a concentration of 10 $\mu$M to increase BK current to 170% of control of IBTX-sensitive current. Recordings were accomplished using standard two-electrode voltage clamp techniques [Stuhmer, W., et al., *Methods in Enzymology*, 207, pp. 319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), $NaHCO_3$ (2.4), KCl (1.0), HEPES (10), $MgSO_4$ (0.82), $Ca(NO_3)_2$ (0.33), $CaCl_2$ (0.41); pH 7.5.

The compound of Formula (S)-II or a prodrug of Formula I was administered intravenous bolus to male Sprague-Dawley rats (n=3 rats/timepoint) at a target dose equivalent to 1 mg/kg of the compound of Formula (S)-II. At T=0.25, 1 and 2 hours post-dose, whole blood samples were collected and extracted with acetonitrile. Blood extracts were analyzed by LC/MS/MS for levels of the compound of Formula (S)-II. Table 1 shows a comparison of estimates of truncated 0.25–2 hours AUC of the compound of Formula (S)-II after administering either the compound of Formula II or the prodrug of Formula I. For example, as shown in Table 1 following the administration of prodrugs of Formula I, the compound of Formula (S)-II was detected in the blood of this rat model.

TABLE 1

Rat Blood Levels of Compound (S)-II after Prodrug Administration

| Example | Truncated Blood $AUC_{(0.25-2\ hr)}$ (ng * hr/mL) Compound of Formula (S)-II |
|---|---|
| Compound of Formula (S)-II | 261 |
| Ia | 48 |

To determine the ability of the compounds of the present invention to reduce cell loss resulting from neuronal ischemia, a standard focal cerebral ischemia is induced by permanent occlusion of the left middle cerebral artery (MCA) and common carotid artery (CCA) with one hour occlusion of the right CCA in the Wistar rat. The surgeries are performed using the sub-temporal approach of A. Tamura, et al., *J. Cereb. Blood Flow Metab.*, 1, pp. 53–60, (1981) and its modifications [K. Osborne, et al., *J. Neurol Neurosurg. Psychiatry*, 50, pp. 402–410 (1987) and S. Menzies, et al., *Neurosurgery*, 31, pp. 100–107, (1992).]

The compound of Formula II was evaluated in the focal stroke model involving permanent occlusion of the left MCA (MCAO) and CCA (CCAO) and temporary occlusion of the right CCA in the Wistar rat [Gribkoff, et al. *Nature Med.* 7, pp. 471–477 (2001)]. This procedure results in a reliably large neocortical infarct volume that is measured by means of vital dye exclusion in serial slices through the brain 24 hours after MCAO. In the present test, compounds were administered using an i.v. or i.p. route of administration two hours after occlusion. For example, in this model the compound of Formula II significantly reduced the cortical infarct volume by about 28% when administered intravenously (0.3 mg//kg) as a single bolus two hours after middle cerebral artery occlusion as compared to vehicle-treated control.

To determine the ability of the compounds of the present invention to decrease the amount of neuronal damage following head injury, a standard model of traumatic brain injury was employed. The rat traumatic brain injury (TBI) model is used to evaluate compounds for effectiveness in reversing or preventing the deleterious effects of a concussion-like injury. In general, rats in this model were anesthetized, a craniotomy is performed (surgical opening of the skull), and then saline was injected into the opening to produce a precise pulse of increased intracranial pressure (commonly called a fluid percussion injury). Animals were administered compound at the specified doses at 15 min following trauma. Animals were euthanized 48 hours post TBI.

Moderate diffuse brain injury (defined by McIntosh, et al. *Neuroscience*, 28:233–44 (1989)) was induced by a fluid-percussion device. The apparatus produces contusion via the rapid injection of a saline pulse [~2.1 to 2.7 atmospheres of pressure (atm)] at a constant duration (21–23 millisecond) into a closed cranial cavity. The saline pulse results in the brief displacement and deformation of the underlying cortex. This model is thought to mimic the clinical situation where a patient experiences a concussion-like injury characterized by brief neurological and systemic physiological alterations without severe structural damage. The fluid percussion device produces brain injury without directly impacting the brain. Diffuse brain injury is achieved by the release of a weighted (4.8 kg) metal pendulum from a predetermined height (McIntosh, et al 1989) that strikes a cork-covered piston at the end of a Plexiglass cylindrical reservoir filled with isotonic saline. Varying volumes of saline are injected into the closed cranial cavity producing a pulse of increased intracranial pressure (ICP). Varying the height of the pendulum controls the magnitude of the injury.

In this experiment the pressure pulses were measured extracranially by a transducer located in the injury device. Following the induction of anesthesia, the trauma screw was tightly connected to the fluid percussion device, and an injury of moderate severity [~2.1 to 2.7 atm], was induced based on a scale established by McIntosh, et al 1989. The pulses were recorded on a storage oscilloscope triggered photoelectrically by descent of the pendulum. Following fluid percussion, the cap created by the trauma screw, the stainless steel screw, and the cranioplastic cement were all removed and the wound closed by non-absorbable suture (3–0). Animals remaining apneic for more than 60 seconds post-injury were immediately euthanatized. Rats were maintained on a water recirculating heating pad until respiration normalized and they were ambulatory. Animals were euthanized and brains removed for assessment of edema at 48 hours by measurement of water content as described previously (McIntosh, et al 1989).

The compound of Formula (S)-II has previously been shown to produce significant reductions in edema in several regions adjacent to the impact zone [Cheney, et al. *J. Cer. Blood Flow & Metab*.21:396–403(2001)].

The results of the above tests demonstrate that the novel oxindoole compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, carbon monoxide poisoning, sexual dysfunction, and urinary incontinence and other disorders sensitive to BK channel activating activity. Most preferably, the compounds of Formula I are useful in the treatment of cerebral ischemia/stroke.

The compounds of Formula I or pharmaceutical compositions thereof are useful in the treatment, alleviation or elimination of disorders or other disorders associated with the BK channels. Such disorders include ischemia, stroke, convulsions, epilepsy, asthma, irritable bowel syndrome, migraine, traumatic brain injury, spinal cord injury, carbon monoxide poisoning, sexual dysfunction and urinary incontinence and other disorders sensitive to potassium channel openers.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 ng/kg to 10 mg/kg body weight. For parenteral administration, the dose may be in the range of 0.1 ng/kg to 10 mg/kg body weight for intravenous administration. The active ingredient will preferably be administered either with a bolus injection or bolus injection followed by continuous infusion; continuously; or in equal doses from one to four times a day.

However, it will be understood that the amount of the compound actually administered will be determined by a physician, in the light of the relevant circumstances, including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

DESCRIPTION OF SPECIFIC EMBODIMENTS

In the following examples, all temperatures are given in degrees Centigrade. Melting points were recorded on a Gallenkamp capillary melting point apparatus temperatures are uncorrected. Proton magnetic resonance ($^1$H NMR), fluorine magnetic resonance ($^{19}$F NMR) and phosphorous magnetic resonance (31P NMR) was recorded on a Bruker Advance 400. All spectra were determined in the solvents indicated and chemical shifts are reported in δ units downfield from an internal standard. Interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M-H)$^-$ was determined on a Finnigen TSO 7000. High resolution mass

EXAMPLE 1

3-(S)-(5-Chloro-2-methoxy-phenyl)-3-fluoro-6-trifluoromethyl-1-(3-(R), 4-(S),5-(S)-trihydroxy-6-(R)-hydroxymethyl-tetrahydro-pyran-2-yloxymethyl)-1,3-dihydro-indol-2-one; 3-(S)-Ia:

Step A: (S)-3-(5-Chloro-2-methoxy-phenyl)-3-fluoro-1-hydroxymethyl-6-trifluoromethyl-1,3-dihydro-indol-2-one; (S)-III.

To a mixture of (S)-3-(5-chloro-2-methoxy-phenyl)-3-fluoro-6-trifluoromethyl-1,3-dihydro-indol-2-one ((S)-II; prepared as described in U.S. Pat. No. 5,808,095) (60.0 g, 0.167 mol) and $K_2CO_3$ (27.7 g, 0.20 mol) in THF (600 mL) was added formaldehyde (37% solution in $H_2O$, 240 mL, 3.2 mol) followed by $H_2O$ (300 mL). The lightly turbid mixture was stirred at room temperature for 3 hours, and diluted with diethyl ether (1000 mL). The organic layer was separated. The aqueous layer was washed with ether (200 mL×2). The combined organic layer was washed with brine, dried over $Na_2SO_4$. Evaporation of solvents provided the title compound as a white dry foam (64.5 g, 99% yield). LC/MS m/e: 390 ($MH^+$), 96% purity. $^1H$ NMR ($CDCl_3$): δ 7.79 (dd, J=1.0, 3.0 Hz, 1H) 7.34 (m, 3H), 7.24 (m, 1H), 6.75 (dd, J=1.5, 6.5 Hz, 1H), 5.45 (m, 1H), 5.28 (m, 1H), 3.50 (s, 3H).

Step B: (S)-3-(5-Chloro-2-methoxy-phenyl)-1-chloromethyl-3-fluoro-6-trifluoromethyl-1,3-dihydro-indol-2-one; (S)-IV:

To a round bottom flask containing alcohol (S)-3-(5-Chloro-2-methoxy-phenyl)-3-fluoro-1-hydroxymethyl-6-trifluoromethyl-1,3-dihydro-indol-2-one ((S)-III) (0.100 g, 0.252 mmol) was added anhydrous dichloromethane (1 mL) and phosphorus trichloride (22 μL, 0.252 mmol). The reaction was allowed to stir overnight at room temperature. The solvent was then removed and the crude product purified via flash chromatography (silica gel, 5:1 hexanes:ethyl acetate) to give the title compound (0.069 g, 66%). $^1H$ NMR ($CDCl_3$, 400 MHz): δ 7.78 (dd, J=1.6 Hz, 1.0 Hz), 7.3 (m, 4H), 6.76 (dd, 1H, J=7.0 Hz, 1.0 Hz), 5.95 (d, 1H, J=11.0 Hz), 5.39 (d, 1H, J=11.0 Hz), 3.55 (s, 3H).

Step C: 3-(S)-(5-Chloro-2-methoxy-phenyl)-3-fluoro-6-trifluoromethyl-1-(3-(R), 4-(S),5-(S)-tris-benzyloxy-6-(R)benzyloxymethyl-tetrahydro-pyran-2-yloxymethyl)-1,3-dihydro-indol-2-one; 3-(S)-VI.

To a round bottom flask containing a solution of (S)-3-(5-Chloro-2-methoxy-phenyl)-1-chloromethyl-3-fluoro-6-trifluoromethyl-1,3-dihydro-indol-2-one (S)-IV (0.486 g, 1.2 mmol) in anhydrous acetonitrile (9 mL) was added 2,3,4,6-tetra-O-benzyl-D-glucopyranose (V; 0.648 g, 1.2 mmol) and cesium carbonate (0.390 g, 1.2 mmol). The reaction mixture was allowed to stir at room temperature overnight. The solvent was then removed, and the crude product was purified via flash chromatography (silica gel, 5:1 hexanes:ethyl acetate) to give a 1:1 mixture of α and β anomers of the title compound (0.768 g, 71%). $^1H$ NMR ($CDCl_3$, 400 MHz): δ 7.79 (dd, 2H, J=5.1 Hz, 1.8 Hz), 7.37–7.12 (m, 48H), 6.66 (m, 2H), 5.66 (d, 1H, J=11.0 Hz), 5.34 (m, 2H), 5.08 (d, 1H, J=3.7 Hz), 4.89–4.73 (m, 9H), 4.66–4.44 (m, 9H), 3.79 (m, 3H), 3.73–3.59 (m, 6H), 3.55–3.49 (m, 3H), 3.38 (d, 6H, J=4.1 Hz).

Step C: 3-(S)-(5-Chloro-2-methoxy-phenyl)-3-fluoro-6-trifluoromethyl-1-(3-(R),4-(S),5-(S)-trihydroxy-6-(R)-hydroxymethyl-tetrahydro-pyran-2-yloxymethyl)-1,3-dihydro-indol-2-one; 3-(S)-Ia:

To a round bottom flask containing a solution of 3-(S)-(5-Chloro-2-methoxy-phenyl)-3-fluoro-6-trifluoromethyl-1-(3-(R),4-(S),5-(S)-tris-benzyloxy-6-(R)benzyloxymethyl-tetrahydro-pyran-2-yloxymethyl)-1,3-dihydro-indol-2-one; (3-(S)-VI) (0.768 g, 0.84 mmol) in 1:1 ethanol:ethyl acetate (6 mL) was added platinum oxide (0.095 g, 0.42 mmol). The reaction was allowed to run at room temperature under a hydrogen atmosphere for 6 days. Once complete, the reaction was filtered through a bed of celite and purified via reverse phase column chromatography ($C_{18}$, 1:1 water:acetonitrile). The title compound was isolated as a white solid (0.279 g, 60%). $^1H$ NMR (MeOH-$D_4$, 400 MHz): δ 7.74 (m, 2H), 7.59 (d, 2H, J=8.8 Hz), 7.41 (m, 4H), 7.30 (dd, 2H, J=5.5 Hz, 2.3 Hz), 6.96 (m, 2H), 5.62 (d, 1H, J=10.8 Hz), 5.55 (d, 1H, J=11.3 Hz), 5.48 (d, 1H, J=10.8 Hz), 5.39 (d, 1H, J=11.2 Hz), 5.07 (d, 1H, J=3.8 Hz), 4.50 (d, 1H, J=7.8 Hz), 3.87 (dd, 1H, J=10 Hz, 1 Hz), 3.68 (m, 4H), 3.54 (d, 6H, J=2.6 Hz), 3.51 (d, 1H, J=4.6 Hz), 3.45 (d, 1H, J=3.8 Hz), 3.43 (d, 1H, J=3.8 Hz), 3.38 (m, 1H), 3.33 (m, 2H), 3.24 (m, 1H ); LRMS: 569 $[M+NH_4]^+$.

EXAMPLE 2

3-(S)-(5-Chloro-2-methoxy-phenyl)-3-fluoro-6-trifluoromethyl-1-(3-(R),4-(S),5-(S)-trihydroxy-6-(R)-hydroxymethyl-tetrahydro-pyran-2-(R)-yl)-1,3-dihydro-indol-2-one; 3-(S)-Ib:

Step A: 1-(4-(S),5-(S)-Bis-benzyloxy-6-(R)-benzyloxymethyl-3-(R)-hydroxy-tetrahydro-pyran-2-(R)-yl)-3-(S)-(5-chloro-2-methoxy-phenyl)-3-fluoro-6-trifluoromethyl-1,3-dihydro-indol-2-one: 3-(S)-VIII To a round bottom flask containing (S)-3-(5-chloro-2-methoxy-phenyl)-3-fluoro-6-trifluoromethyl-1,3-dihydro-indol-2-one ((S)-II) (0.200 g, 0.55 mmol) was added anhydrous tetrahydrofuran (3 mL) and 95% sodium hydride (0.018 g, 0.7 mmol). The yellow solution was allowed to stir at room temperature for 30 minutes. 1,2-Anhydro-3,4,6-tri-O-benzyl-α-D-glucopyranose (prepared by the method of Halcomb and Danishefsky *J. Am. Chem. Soc.* 1989, 111, 6661) (0.480 g, 1.1 mmol) was then dissolved in anhydrous tetrahydrofuran (2.5 mL) and added dropwise to the reaction mixture over 15 minutes. The reaction was allowed to stir at reflux overnight. Once complete, the reaction was cooled and then poured into saturated sodium bicarbonate. The solution was extracted with ethyl acetate (3×). The organic layer was washed with brine and then dried over anhydrous sodium sulfate. The crude mixture was purified via flash chromatography (silica gel, 30% ethyl acetate in hexanes). The title product was obtained as a yellow oil (0.287 g, 65%). $^1H$ NMR ($CDCl_3$, 400 MHz): δ 7.79 (dd, 1H, J=1.8 Hz, 0.68 Hz), 7.45 (s, 1H), 7.39–7.20 (m, 18H), 6.69 (dd, 1H, J=7.6 Hz, 1.1 Hz), 5.43 (d, 1H, J=9.5 Hz), 4.93 (m, 3H), 4.67 (m, 1H), 4.55 (dd, 2H, J=12.3 Hz, 5.7 Hz), 4.3 (ddd, 1H, J=4.9 Hz, 4.2 Hz), 3.87 (d, 1H, J=9.3 Hz), 3.79–3.70 (m, 4H), 3.42 (s, 3H), 2.54 (d, 1H, J=4.3 Hz).

Step B: 3-(S)-(5-Chloro-2-methoxy-phenyl)-3-fluoro-6-trifluoromethyl-1-(3-(R),4-(S),5-(S)-trihydroxy-6-(R)-hydroxymethyl-tetrahydro-pyran-2-(R)-yl)-1,3-dihydro-indol-2-one; 3-(S)-Ib:

To a round bottom flask containing 1-(4-(S),5-(S)-Bis-benzyloxy-6-(R)-benzyloxymethyl-3-(R)-hydroxytetrahydro-pyran-2-(R)-yl)-3-(S)-(5-chloro-2-methoxy-phenyl)-3-fluoro-6-trifluoromethyl-1,3-dihydro-indol-2-one ((S)-VIII) (0.144 g, 0.18 mmol) was added ethyl acetate (1 mL). Platinum oxide (0.020 g, 0.09 mmol) was added to the reaction mixture which was then placed under a hydrogen atmosphere. The reaction was allowed to stir at room temperature overnight. The crude reaction mixture was purified via reverse phase column chromatography ($C_{18}$, 1:1 water:acetonitrile). The title product was obtained as a white solid (0.040 g, 42%). $^1$H NMR (MeOH-$D_4$, 400 MHz): δ 7.73 (dd, 1H, J=1.6 Hz, 0.9 Hz), 7.52 (s, 1H), 7.39 (m, 2H), 7.30 (dd, 1H, J=5.5 Hz, 2.0 Hz), 6.94 (dd, 1H, J=7.5 Hz, 1.2 Hz), 5.43 (d, 1H, J=9.5 Hz), 4.04 (t, 1H, J=9.1 Hz), 3.95 (dd, 1H, J=10.5 Hz, 1.4 Hz), 3.75 (dd, 1H, J=6.8 Hz, 5.3 Hz), 3.57 (s, 3H), 3.53 (m, 2H); $^{19}$F NMR (MeOH-$D_4$, 376 MHz): δ−64.6, −161.7; LRMS: 519 [M−H]$^-$.

EXAMPLE 3

Phosphoric acid mono-{2-(R)-[3-(S)-(5-chloro-2-methoxy-phenyl)-3-fluoro-2-oxo-6-trifluoromethyl-2,3-dihydro-indol-1-yl]-4-(S),5-(S)-dihydroxy-6-(R)-hydroxymethyl-tetrahydro-pyran-3-(R)-yl}ester, 3-(S)-Ic:

Step A: Phosphoric acid dibenzyl ester 4-(S),5-(S)-bis-benzyloxy-6-(R)-benzyloxymethyl-2-(R)-[3-(S)-(5-chloro-2-methoxy-phenyl)-3-fluoro-2-oxo-6-trifluoromethyl-2,3-dihydro-indol-1-yl]-tetrahydro-pyran-3-(R)-yl ester; 3-(S)-IX:

To a round bottom flask containing 1-(4-(S),5-(S)-Bis-benzyloxy-6-(R)-benzyloxymethyl-3-(R)-hydroxy-tetrahydro-pyran-2-(R)-yl)-3-(S)-(5-chloro-2-methoxy-phenyl)-3-fluoro-6-trifluoromethyl-1,3-dihydro-indol-2-one (3-(S)-VIII) (0.048 g, 0.06 mmol) was added 1H-tetrazole (0.026 g, 0.37 mmol), 4-(dimethylamino)-pyridine (0.006 g, 0.049 mmol), and anhydrous dichloromethane (1 mL). The solution was stirred at room temperature and dibenzyl diisopropyl phosphoramidate (0.084 g, 0.24 mmol) was added dropwise. The reaction mixture was allowed to stir at room temperature for 24 hours. 30% aqueous hydrogen peroxide (1 mL) was added and the reaction was allowed to run at room temperature for another 3 hours. The mixture was then separated into layers. The organic layer was washed with distilled water (3×) and dried over anhydrous sodium sulfate. The crude material was purified via flash chromatography (silica gel, 20% ethyl acetate in hexanes) yielding the title product (0.045 g, 71%) as a clear and colorless oil. $^1$H NMR (CDCl$_3$, 400 MHz): δ 7.78 (dd, 1H, J=1.72 Hz, 0.8 Hz), 7.45–7.21 (m, 25H), 7.13 (m, 2H), 7.06 (dd, 2H, J=5.8 Hz, 2.0 Hz), 6.68 (dd, 1H, J=7.6 Hz, 1.2 Hz), 5.71 (d, 1H, J=9.4 Hz), 5.02–4.75 (m, 7H), 4.63 (m, 2H), 4.49 (m, 2H), 3.87 (m, 2H), 3.72–3.65 (m, 3H), 3.34 (s, 3H).

Step B: Phosphoric acid mono-{2-(R)-[3-(S)-(5-chloro-2-methoxy-phenyl)-3-fluoro-2-oxo-6-trifluoromethyl-2,3-dihydro-indol-1-yl]-4-(S),5-(S)-dihydroxy-6-(R)-hydroxymethyl-tetrahydro-pyran-3-(R)-yl}ester; 3-(S)-Ic:

To a round bottom flask containing Phosphoric acid dibenzyl ester 4-(S),5-(S)-bis-benzyloxy-6-(R)-benzyloxymethyl-2-(R)-[3-(S)-(5-chloro-2-methoxy-phenyl)-3-fluoro-2-oxo-6-trifluoromethyl-2,3-dihydro-indol-1-yl]-tetrahydro-pyran-3-(R)-yl ester (3-(S)-IX) (0.117 g, 0.11 mmol) was added ethyl acetate (1 mL). Platinum oxide (0.013 g, 0.06 mmol) was added to the reaction mixture which was then placed under a hydrogen atmosphere. The reaction was allowed to stir at room temperature overnight. The crude reaction mixture was purified via reverse phase column chromatography ($C_{18}$, 1:1 water:acetonitrile). The title product was obtained as a white solid (0.045 g, 68%). $^1$H NMR (MeOH-$D_4$, 400 MHz): δ 7.72 (d, 1H, J=1.8 Hz), 7.5 (s, 1H), 7.38 (dd, 1H, J=6.2 Hz, 2.6 Hz), 7.29 (dd, 1H, J=21.7 Hz, 7.7 Hz), 6.93 (dd, 1H, J=7.7 Hz, 1.1 Hz), 5.61 (d, 1H, J=9.4 Hz), 3.97 (d, 1H, J=11.9 Hz), 3.77 (m, 2H), 3.57 (s, 3H); $^{19}$F NMR (MeOH-$D_4$, 376 MHz): δ−64.5, −163.3; 31P NMR (MeOH-$D_4$, 161 MHz): δ 1.54; LRMS: 599 [M−H]$^-$.

What is claimed is:

1. A compound of the formula

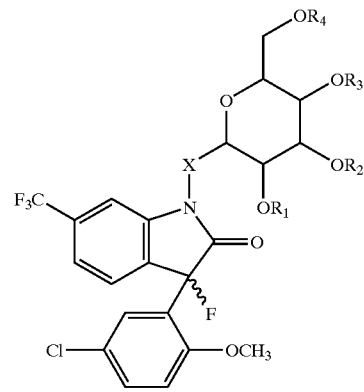

wherein the wavy bond (⁓) represents the racemate, the (R)-enantiomer or the (S)-enantiomer;

$R_1$, $R_2$, $R_3$ and $R_4$ each are independently hydrogen or —P(O)OR$^5$OR$^6$;

$R^5$ and $R^6$ each are independently hydrogen or $C_{1-4}$ alkyl;

X is a covalent bond or —CR$^5$R$^6$O—;

or a nontoxic pharmaceutically acceptable salt or solvate thereof.

2. The compound of claim 1 which is 3-(S)-(5-Chloro-2-methoxy-phenyl)-3-flucro-6-trifluoromethyl-1-(3-(R), 4-(S), 5-(S)-trihydroxy-6-(R)-hydroxymethyl-tetrahydro-pyran-2-yloxymethyl)-1,3-dihydro-indol-2-one or a pharmaceutically acceptable salt or solvate thereof.

3. The compound of claim 1 which is 3-(S)-(5-Chloro-2-methoxy-phenyl)-3-fluoro-6-trifluoromethyl-1-(3-(R), 4-(S), 5-(S)-trihydroxy-6-(R)-hydroxymethyl-tetrahydro-pyran-2-(R)-yl)-1,3-dihydro-indol-2-one or a pharmaceutically acceptable salt or solvate thereof.

4. The compound of claim 1 which is phosphoric acid mono-{2-(R)-[3-(S)-(5-Chloro-2-methoxy-phenyl)-3-fluoro-2-oxo-6-trifluoromethyl-2,3-dihydro-indol-1-yl]-4-(S), 5-dihydroxy-6-(R)-hydroxymethyl-tetrahydro-pyran-3-(R)-yl} ester or a pharmaceutically acceptable salt or solvate thereof.

5. A pharmaceutical composition for the treatment of disorders responsive to openers of the large conductance calcium-activated potassium channels, the disorders consisting of cerebral ischemia and stroke with the composition comprising a therapeutically effective amount of a compound of defined in claim 1 in association with a pharmaceutically acceptable carrier or diluent.

6. A method for the treatment of disorders responsive to opening of the large conductance calcium-activated potassium channels in a mammal in need thereof, the disorders consisting of cerebral ischemia and stroke and the method comprises administering to said mammal a therapeutically effective amount of a compound us defined in claim 1.

7. The method of claim 6 wherein the disorder is stroke.

8. The method of claim 6 wherein the disorder is cerebral ischemia.

* * * * *